(12) United States Patent
Seo

(10) Patent No.: US 9,861,529 B2
(45) Date of Patent: Jan. 9, 2018

(54) MASK REMOVABLE TYPE AUTOMATIC SHADING GOGGLES

(71) Applicant: SERVORE CO., LTD., Pyeongtaek-si, Gyeonggi-do (KR)

(72) Inventor: Woon Su Seo, Gwangmyeong-si (KR)

(73) Assignee: SERVORE CO., LTD., Gyeonggi-Do (KR)

( * ) Notice: Subject to any disclaimer, the term of this patent is extended or adjusted under 35 U.S.C. 154(b) by 338 days.

(21) Appl. No.: 14/205,560

(22) Filed: Mar. 12, 2014

(65) Prior Publication Data

US 2014/0259252 A1    Sep. 18, 2014

(30) Foreign Application Priority Data

Mar. 12, 2013    (KR) .......................... 10-2013-0025926

(51) Int. Cl.
| | |
|---|---|
| *A61F 9/01* | (2006.01) |
| *F41H 1/00* | (2006.01) |
| *G09G 5/00* | (2006.01) |
| *A61F 9/02* | (2006.01) |

(52) U.S. Cl.
CPC .................................... *A61F 9/022* (2013.01)

(58) Field of Classification Search
CPC .......... A61F 9/022; A61F 9/023; A61F 9/024; A61F 9/025; A61F 9/00; A61F 9/29; A42B 3/14; A42B 3/142; A42B 3/147

USPC ..................................... 2/8.2, 455; 345/8, 87
See application file for complete search history.

(56) References Cited

U.S. PATENT DOCUMENTS

| | | | | |
|---|---|---|---|---|
| 3,298,031 A | * | 1/1967 | Morgan ............. | A41D 13/1184 2/427 |
| 5,247,706 A | * | 9/1993 | Mark ...................... | A61F 9/025 2/13 |
| 5,463,428 A | * | 10/1995 | Lipton ............... | G02B 27/2264 348/E13.04 |
| 5,802,622 A | * | 9/1998 | Baharad ................... | A61F 9/02 2/2.5 |
| 5,966,738 A | * | 10/1999 | Wang Lee ............. | A42B 3/225 2/10 |
| 6,948,813 B2 | * | 9/2005 | Parks ...................... | A61F 9/025 2/436 |
| 8,081,262 B1 | * | 12/2011 | Perez ...................... | A61F 9/023 2/8.1 |

* cited by examiner

*Primary Examiner* — Khaled Annis
*Assistant Examiner* — Timothy K Trieu
(74) *Attorney, Agent, or Firm* — IPLA P.A.; James E. Bame

(57) ABSTRACT

Provided are mask removable type automatic shading goggles in that a welding helmet is manufactured in a goggle shape, so that the mask removable type automatic shading goggles can replace the existing heavy and large welding surface; the mask removable type automatic shading goggles can also be used for both an arc welding work and a grinding work, a cutting work, and a gas welding work; and if necessary, the mask part can be easily attachably and detachably coupled to the goggle part.

4 Claims, 5 Drawing Sheets

MASK REMOVABLE TYPE AUTOMATIC SHADING GOGGLES

CROSS REFERENCE

Applicant claims foreign priority under Paris Convention to Korean Patent Application No. 10-2013-0025926, filed 12 Mar. 2013, with the Korean Intellectual Property Office, where the entire contents are incorporated herein by reference.

BACKGROUND OF THE INVENTION

1. Field of the Invention

The present invention relates to mask removable type automatic shading goggles, and more particularly to mask removable type automatic shading goggles in that a welding helmet is manufactured in a goggle shape, so that it can replace the existing heavy and large welding surface; it can also used for both an arc welding work and a grinding work, a cutting work, and a gas welding work; and if necessary, the mask part can be easily attachably and detachably coupled to the goggle part.

2. Description of the Prior Art

Generally, the welding is a technique of jointing same or different kinds of metal materials by partially applying a heat and a pressure to them at the same time. During the welding, since a strong light (arc) is emitted and broken pieces are generated, where the worker's eye is exposed to the strong light, it can cause loss of vision of the worker and inflict an injury on his eyeball etc. owing to the broken pieces.

Accordingly, in industrial settings, the work wears a welding helmet for protecting the eyeball and faces thereof from the strong light or broken pieces generated during the welding operation or cutting operation etc.

FIG. 1 is a schematic perspective view illustrating a conventional welding helmet.

As shown in FIG. 1, the conventional welding helmet includes a welding mask 210 for covering the entire face of the wearer, a wearing band 220 for wearing the welding mask 210 on a head of the wearer and rotating the welding mask 210 at a predetermined angle upward and downward and coupled to the welding mask 210 through a rotating axis 221, a light detecting sensor (not shown) for detecting the strong light and generating a driving signal during the generation of the strong light formed at one side of the welding mask 210, a liquid crystal display (LCD) cartridge 230 for protecting the eye of the wearer from the strong light generated during the operation thereof by varying the shading degree of shading the light according the driving signal and formed at a location corresponding to the eye of the wearer, and a front cover 240 for protecting the LCD cartridge 230 and formed at the front side of the LCD cartridge 230.

According to the conventional welding helmet, where the strong light (arc) is generated during the welding operation, the light detecting sensor detects the strong light and generates the driving signal and the light transmission of the LCD cartridge 230 becomes lower according to the generated driving signal to block the strong light.

By the way, since the conventional welding helmet is manufactured to a comparatively large size for covering the face of the worker, it lays heavy strain on the neck of the worker owing to the weight thereof and the storage is not easy owing to the big size thereof.

Also, as described above, in the conventional welding helmet, in order to block the strong light generated during the welding operation, since the light transmission of the LCD cartridge 230 is remarkably lowered, there is a problem in that it is difficult to distinguish the surrounding objects.

Accordingly, where the worker intends to combine the welding operation with another operation, since the attaching and deattaching operations of the welding helmet are repeatedly performed, it is quite cumbersome to do. Also, in case of a manager in a work zone of managing various operations at the same time, in a state that the worker grasps the eye shield for protecting his eye from the broken pieces of the metalwork and the strong visible rays and the welding helmet for protecting his eye from the strong light generated during the welding operation, since he selectively uses the eye shield and the welding helmet, it is quite cumbersome to do. Moreover, because he purchases the eye shield and the welding helmet separately, the financial burden is increased owing to the purchase thereof. Furthermore, since the eye shield and the welding helmet are stored separately, there is a problem in that is very cumbersome to maintain them.

SUMMARY OF THE INVENTION

Accordingly, the present invention has been made to solve the above-mentioned problems occurring in the prior art, and an object of the present invention is to provide mask removable type automatic shading goggles in that a welding helmet is manufactured in a goggle shape, so that the size thereof is compact and the weight thereof is light, and a mask is attachably and detachably coupled thereto, so that the working convenience is increased.

Another object of the present invention is to provide mask removable type automatic shading goggles in that a power is supplied to a LCD lens and a control panel by means of an electrical connection panel longitudinally formed on an inside body, so that it can prevent the cutoff of the power supply owing to the movement of the conventional power line, thereby prevent a malfunction due to a noise of a sense line.

Further another object of the present invention is to provide mask removable type automatic shading goggles in that air vents are formed at one side of the front body, so that the air is circulated to the inside and outside of the skirt part, thereby it can previously prevent the condensation from being occurred on the LCD lens owing to the heat generated from an eyeball of the worker.

To accomplish the object, the present invention provides mask removable type automatic shading goggles including: a goggle part having a LCD lens for blocking a harmful light and protecting a worker's eye installed on an inside thereof and closely worn to a worker's face; and a mask part having a cover body corresponded to a front surface of the goggle part and attachably and detachably coupled to the front surface of the goggle part, and a face protective cover for protecting the worker's face extended to a lower portion of the cover body.

Preferably, the mask part further includes a supporting jaw having a surface bent between the cover body and the face protecting cover and closely supporting an upper end or a lower end of the goggle part.

Preferably, the mask removable type automatic shading goggles further includes a hooking part extended from one side of an upper end of the cover body toward an upper end of goggle part so as to be coupled to an upper end portion of the goggle part.

Preferably, the mask removable type automatic shading goggles further includes a pair of locking walls as an extending side wall extended from both sides of the cover body to the rear of the cover body and having exposure holes for exposing both side surfaces of the goggle part to outside, so that, when the mask part is coupled to the goggle part, the pair of locking walls is slid to both sides of the goggle part while being opened to outside, whereby the pair of locking walls is elastically coupled to both sides of the goggle part.

Preferably, the goggle part further includes a skirt part of a soft material coupled to a rear surface of the goggle part and adhered to the worker's face and the skirt part includes a tightly contacting part corresponding to an outer circumference shape of the rear surface of the goggle part and adhered to the rear surface of the goggle part; a coupling part corresponded to the inner surface of the goggle part and protruded from the front surface of the tightly contacting part toward the front part thereof; a curve supporting surface having openings corresponded to a LCD lens at the front surface of the coupling part and extended along an outer circumference of the openings and bent and bordered on the coupling part; and a supporting plate corresponded to the curve supporting surface and closely coupled to the inside of the curve supporting surface.

Preferably, the goggle part further includes: extending side walls extended from both end portions thereof and the rear thereof; a control panel formed at one side of the side walls, supplying a voltage to a LCD lens, and varying a light transmission of the LCD lens; a power supply formed at one side of the goggle part and supplying a power to the control panel; and an electrical connection panel formed at the inside of the goggle part and having one end electrically connected to the power supply and the other end electrically connected to the control panel, wherein the power is supplied to the LCD lens and the control panel by means of the electrical connection panel.

Preferably, the goggle part further includes: an inside body formed in a shape corresponding to a curvature of a worker's face and having a pair of first extending side walls extended from both sides thereof to the rear thereof so as to an installation and first openings formed at the front surface thereof; a front body formed at a front surface of the inside body and having second openings corresponding to the first openings and a pair of second extending side walls extended from both sides thereof to the rear thereof and corresponded to the pair of the first extending side walls respectively and first exposure holes formed on one side of the pair of the second extending side walls so as to expose parts of the control panel and the power supply to outside; and the LCD lens for covering the first openings interposed between the inside body and the front body; openings, wherein the front body further comprises at least one ventilation part formed on one side thereof.

Preferably, the ventilation part includes a plurality of air vents formed on the upper and lower portions of the front body or one side of the second extending side walls so as to allow the air to be circulated to the inside and outside of the front body.

BRIEF DESCRIPTION OF THE DRAWINGS

The above as well as the other objects, features and advantages of the present invention will be more apparent from the following detailed description taken in conjunction with the accompanying drawings, in which.

DETAILED DESCRIPTION OF THE INVENTION

Hereinafter, preferred embodiments of the present invention will be described with reference to the accompanying drawings.

Figure 1:
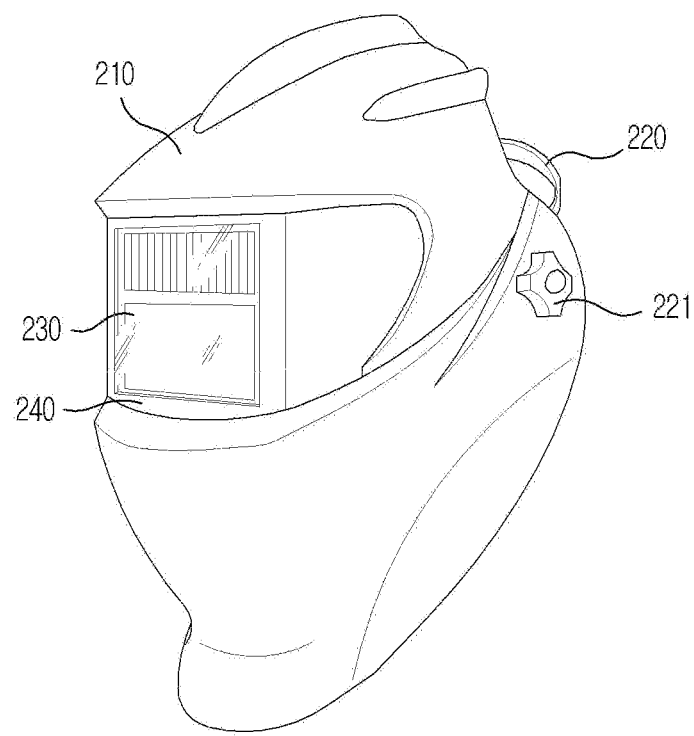
FIG. 1 is a schematic perspective view illustrating a conventional welding helmet.
Figure 2:
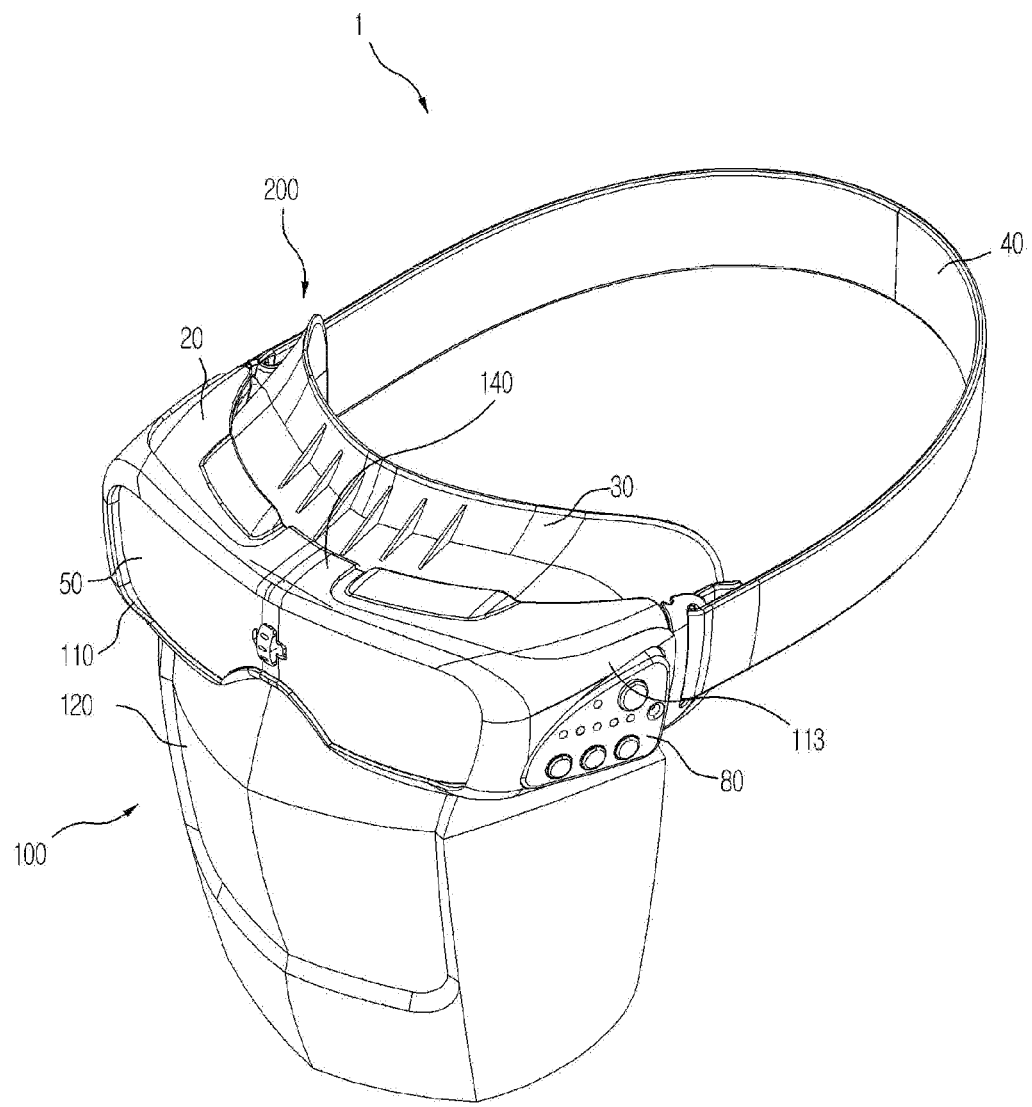
FIG. 2 is a front perspective view illustrating mask removable type automatic shading goggles according to the present invention.
Figure 3:
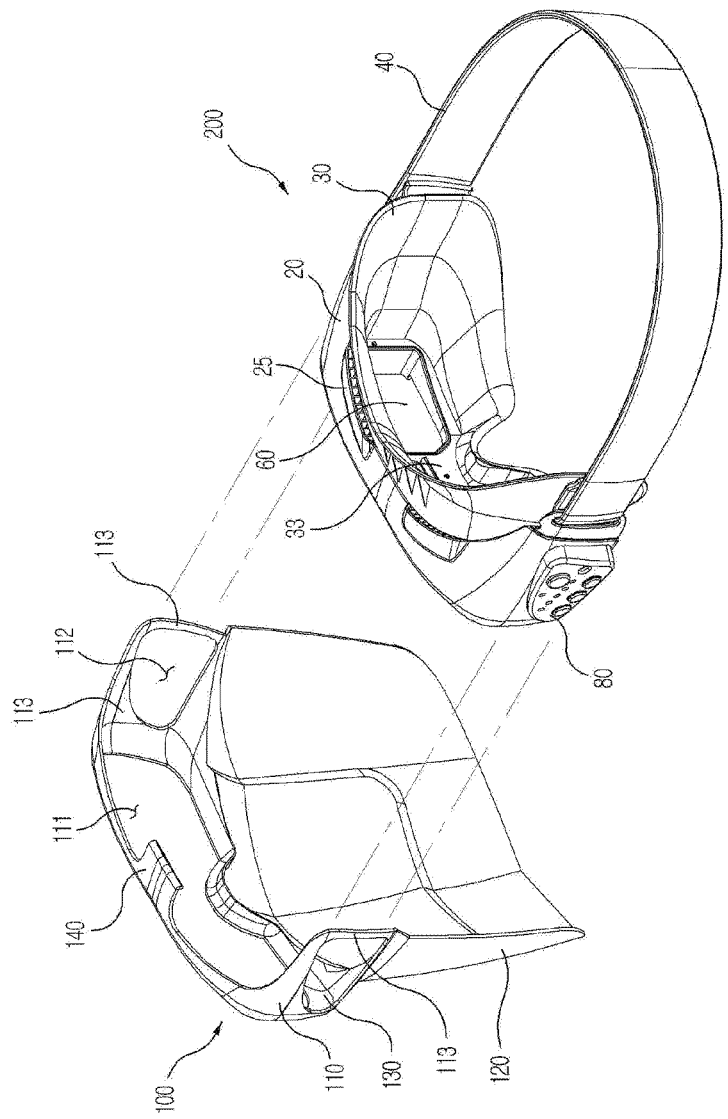
FIG. 3 is a perspective view illustrating a status in that the mask part and the goggle part are separated from each other.
Figure 4:
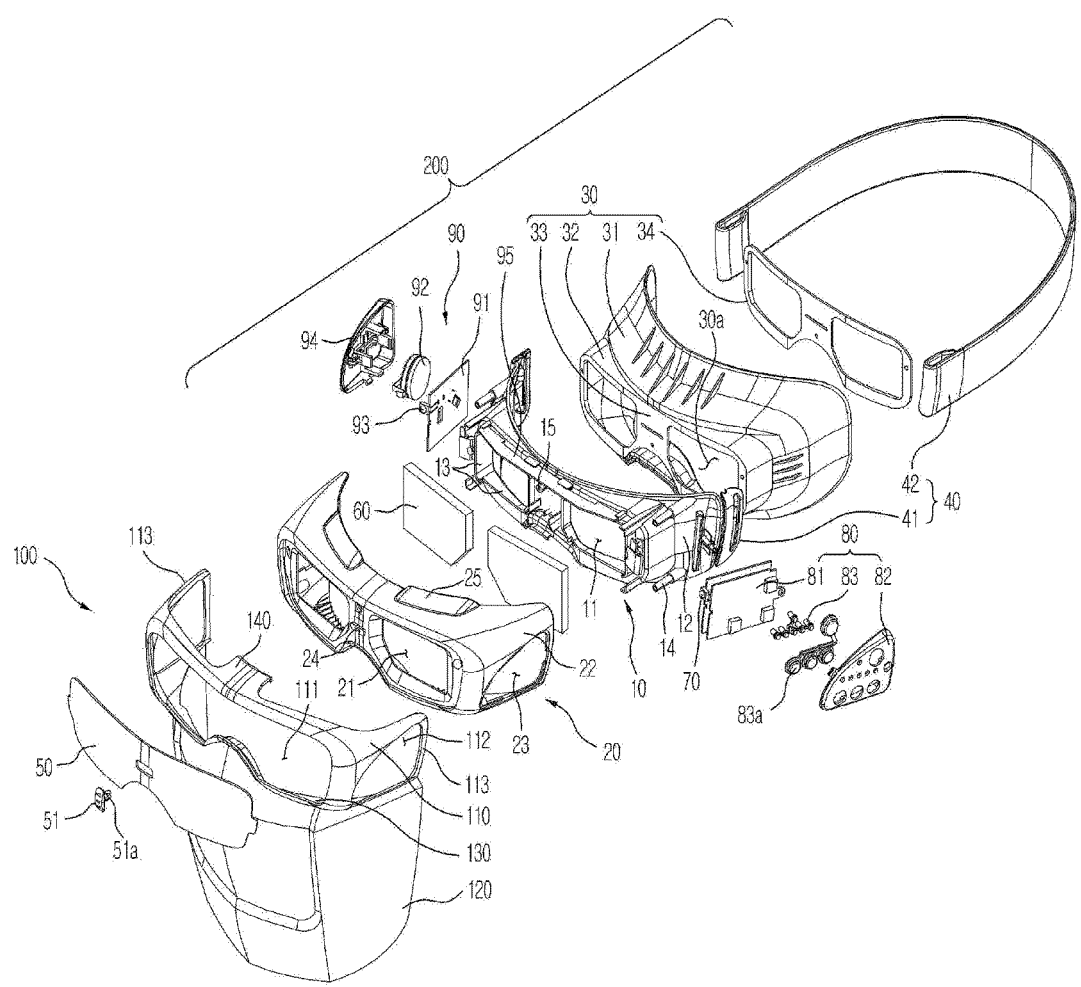
FIG. 4 is a front exploded perspective view illustrating mask removable type automatic shading goggles according to the present invention.
Figure 5:
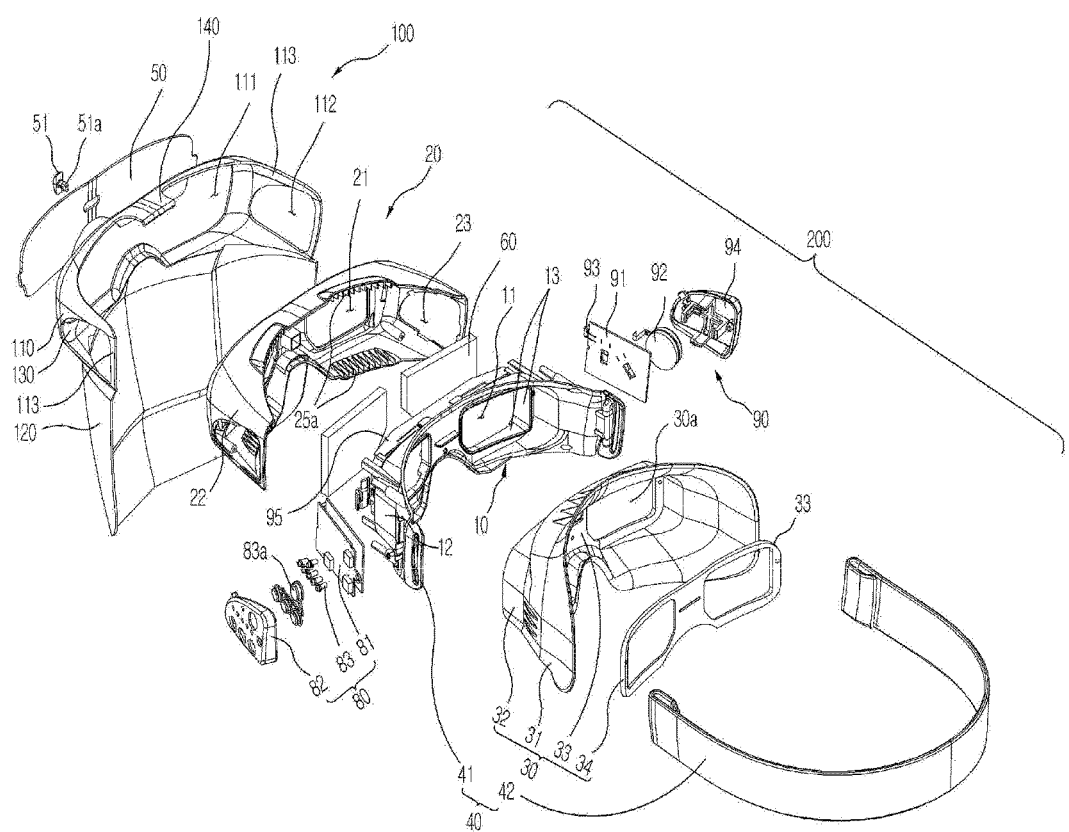
FIG. 5 is a rear exploded perspective view illustrating mask removable type automatic shading goggles according to the present invention.

FIG. 2 is a front perspective view illustrating mask removable type automatic shading goggles according to the present invention, FIG. 3 is a perspective view illustrating a status in that the mask part and the goggle part are separated from each other, FIG. 4 is a front exploded perspective view illustrating mask removable type automatic shading goggles according to the present invention, and FIG. 5 is a rear exploded perspective view illustrating mask removable type automatic shading goggles according to the present invention.

Referring to the drawings, the mask removable type automatic shading goggles according to the present invention includes a goggle part 200 having a LCD lens 60 for blocking a harmful light and protecting a worker's eye installed on an inside thereof and adhered and worn to a worker's face; and a mask part 100 having a cover body 110 corresponded to a front surface of the goggle part 200 and attachably and detachably coupled to the front surface of the goggle part 200 and a face protective cover 120 for protecting a worker's face extended to a lower portion of the cover body 110.

The goggle part 200 includes an inside body 10 corresponded to a flection of the worker's face and a pair of first extending side walls 12 extended from both sides thereof to the rear thereof; a light detecting sensor 70 formed at one side of the inside body 10 and detecting a light and generating a driving signal when the light more than a previous set value is generated; a control panel 80 formed on one first extending side wall 12; a power supply 90 formed on the other first extending side wall 12; a front body 20 coupled to a front surface of the inside body 10; a skirt part 30 of a soft material coupled to a rear surface of the inside body 10 and adhered to the worker's face; a fixing member 40 coupled to both side ends of the inside body 10 and fixed to a head part of the worker; and the LCD lens 60 interposed between the inside body 10 and the front body 20.

The inside body 10 includes a pair of first openings 11 in front and a pair of first extending side walls 12 extended from both sides thereof to the rear thereof. The inside body 10 serves to provide an installation space of the LCD lens 60, the control panel 80, and the power supply 90.

Also, the inside body 10 includes a plurality of fixing pieces 13 corresponded to an outer circumference of the LCD lens 60 for covering the pair of first openings 11 formed on the front thereof and protruded from one side to the front portion thereof.

The fixing piece 13 is formed at one side of the front surface of the inside body 10. The fixing piece 13 serves to support one side of the outer circumference of the LCD lens 60 and allow the LCD lens 60 to be arranged on the front portion of the inside body 10.

Moreover, the inside body 10 further includes a plurality of coupling pillars 14 coupled to the front body 20 and extended from one side of an outside surface of the first extending side walls 12 to the front thereof and a plurality of coupling holes 15 formed on one side of the front portion thereof and coupled to the following skirt part 30 by means of a screw.

The front body 20 includes a pair of second openings 21 corresponding to the first openings 11 in front and a pair of second extending side walls 22 extended from both sides thereof to the rear thereof and corresponded to the pair of the first extending side walls 12 respectively and first exposure holes 23 formed on one side of the pair of the second extending side walls 22 so as to expose a cover of the control panel 80 and a cover of the power supply 90 to outside.

The front body 20 includes a coupling recess 24 formed between the pair of the second openings 21 and coupled to a coupling protrusion 51a of the following protective lens fastener 51.

The above front body 20 serves to form an external shape in general and provide an installation space of a protective lens 50 so as to install the protective lens 50 therein.

Also, the front body 20 further includes ventilation parts 25 formed on one side thereof so as to allow the internal air of the front body to be circulated.

More concretely, at least one air vent 25a is formed on an upper part and a lower part of the front body or one side of the second extending side walls 22 so as to allow the air to be circulated to the inside and outside of the front body 20 through the air vents 25a, thereby it can previously prevent the condensation from being occurred on the following LCD lens 60 owing to the heat generated from an eyeball of the worker.

The pair of the LCD lens 60 having a plate shape is arranged on the front surface of the inside body 10 and the outer circumference of the LCD lens 60 is supported by the plurality of the fixing pieces 13. Here, where the front body 20 is coupled to the inside body 10, the outer circumference area of the front surface of the LCD lens 60 is supported by and fixed to one side of the inner surface of the front body 20.

The light detecting sensor 70 is formed at the control panel 80 and the power supply 90 one by one. The light detecting sensor 70 serves to detect a light generated from outside and generate a driving signal.

The control panel 80 includes a control printed circuit board 81 electrically connected to the LCD lens 60 and the light detecting sensor 70, a first cover 82 for covering the control printed circuit board 81 coupled to one side of the inside body 10 corresponding to the control printed circuit board 81, a shading degree adjusting part 83 having one end portion exposed to outside and another end portion electrically contacted to one side of the control printed circuit board 81, so that the shading degree of the LCD lens 60 can be controlled.

Here, the control printed circuit board 81 receives the driving signal from the light detecting sensor 70 and supplies the voltage to the LCD lens 60, so that the LCD lens 60 can be driven in the security mode or the welding mode.

The power supply 90 includes a power printed circuit board 91 electrically connected to the LCD lens 60 and the control printed circuit board 81 to supply the power thereto, a battery 92 contacted to the power printed circuit board 91, a light emitting diode 93 formed on one side of the inside body 10, and a second cover 94 for covering the power printed circuit board 91 coupled to one side of the inside body 10 corresponding to the power printed circuit board 91.

The power supply 90 serves to supply the power to the LCD lens 60 and the control printed circuit board 81 and detect the voltage of the battery below the pre-set voltage value to display a low voltage through the light emitting diode 93.

Also, the power supply 90 includes a power button for turning on or turning off the power.

An electrical connection panel 95 is electrically connected to one side of the power supply 90 and electrically connected to one side of the control panel. The electrical connection panel 95 is longitudinally formed on the upper end portion of the inside body 10. Accordingly, the power is supplied to the LCD lens 60 and the control panel 80 by means of the electrical connection panel 95. In this case, when the power is supplied by a common power supply line, the power supply line can be disconnected owing to the movement thereof. However, in the present invention, it can prevent the cutoff of the power supply in the LCD lens 60 and the control panel 80 by means of the electrical connection panel 95.

Also, the electrical connection panel 95 allows the LCD lens 60 and the control panel 80 to be electrically connected, so that it can prevent a malfunction due to a noise of a sense line.

Moreover, the electrical connection panel 95, which is longitudinally installed thereon, may be a typical PCB or a flexible PCB according to circumstances.

Furthermore, the control panel 80 and the power supply 90 are exposed to outside through the first exposure holes 23, the cover of the control panel 80 and the cover of the power supply 90, so that the component parts of the control panel 80 and the power supply 90 can be easily changed or repaired.

Also, the operating switch of the control panel 80 and the power supply 90 are exposed to outside through the first exposure holes 23 as described above, or exposed to the upper portion of the second extending side walls 22 of the front body 20, so that the worker can easily manipulated.

The skirt part 30 made of a soft silicon includes a tightly contacting part 31 corresponding to an outer circumference shape of the rear surface of the inside body 10, a coupling part 32 corresponded to the inner surface of the inside body 10 and protruded from the front surface of the tightly contacting part 31 toward the front part thereof, a curve supporting surface 33 having openings 30a corresponded to the LCD lens 60 at the front surface of the coupling part 32, and extended along an outer circumference of the openings and bent and bordered on coupling part 32, and a supporting plate 34 corresponded to the curve supporting surface 33 and closely coupled to the inside of the curve supporting surface 33.

Accordingly, the supporting plate 34 is bordered on the inside surface of the curve supporting surface 33 and the screw holes are continuously penetrated through the inside surface of the supporting plate 34, the curve supporting surface 33, and the inside body 10, so that the supporting plate 34 is screw-coupled to the inside surface of the inside body 10.

The above skirt part 30 made of the soft silicon can be block the harmful light or fumes etc. Also, the above skirt part 30 is adhered to the worker's face, thereby improving the cushion function and the wearing sensation. Since the skirt part 30 is coupled to the inside body by means of the supporting plate 34, the replacement thereof is easy.

The fixing member 40 includes a pair of hooks 41 coupled to both side surfaces of the inside body 10 respectively and a band part 42 of an elastic material having both end parts coupled to the pair of hooks 41 respectively. The band part 42 is fixed to the head of the worker, so that the rear surface of the skirt part 30 can be adhered to the face of the worker.

The mask part 100 includes a cover body 110 attachably and detachably coupled to the front body 20 and a face protecting cover 120 extended to a lower portion of the cover body 110.

The cover body 110 corresponding to the front body 20 includes a pair of third openings 111 corresponding to the second openings 21 in front and a pair of locking walls 113 as an extending side wall extended from both sides thereof to the rear thereof, and second exposure holes 112 corresponded to the first exposure holes 23 so as to expose the control panel 80 and the power supply 90 to outside. The pair of locking walls are provided as an extending side wall extended from both sides of the cover body to the rear of the cover body and having exposure holes for exposing both side surfaces of the goggle part to outside of the mask removable automatic shading goggles, so that, when the mask part is coupled to the goggle part, the pair of locking walls is slid to both sides of the goggle part while being opened to outside of the mask removable automatic shading goggles, whereby the pair of locking walls is elastically coupled to both sides of the goggle part.

In the drawings, when the mask part 100 is coupled to the goggle part 200, the pair of locking walls 113 is slid to the rear of the goggle part 200 while being bordered on both sides the goggle part 200 and being opened to outside and the control panel 80 and the power supply 90, which is formed at both sides of the goggle part 200 are exposed to outside through the second exposure holes 112. That is, the pair of locking walls 113 is elastically coupled to both sides of the goggle part 200.

As described above, the control panel 80 and the power supply 90 are exposed to outside through the second exposure holes 112. However, additionally, a battery cover or a cover of the control panel can be coupled to both sides of the goggle part 200. That is, these covers are exposed to outside through the second exposure holes 112 while the pair of locking walls 113 is coupled to both sides of the goggle part 200.

The face protecting cover 120 serves to cover the lower portion of the worker's eyeball. Also, the face protecting cover 120 is integrally and detachably coupled to the cover body 110.

Also, the mask part 100 further includes a supporting jaw 130 having a surface bent between the cover body 110 and the face protecting cover 120 and closely supporting an upper end or a lower end of the front body 20 thereon. The supporting jaw 130 serves to increase the adhesive force between the mask part 100 and the front body 20 and block the harmful light, which can be flowed from the lower end of the front body 20.

Moreover, the mask part 100 further includes a hooking part 140 extended from one side of the upper end thereof toward the upper end of the goggle part 200 and coupled and attached to the upper end portion of the goggle part 200.

More concretely, the hooking part 140 is protruded from the upper end of the cover body 110 to the rear thereof and includes an end portion, which is bent downward, is inserted into and coupled to the upper end of the goggle part 200.

The protective lens 50 is made of a transparent material and formed at one side of the front surface of the front body 20 so as to block the second openings 21 and the third openings 111, so that it can previously prevent the following LCD lens 60 from being damaged owing to the broken pieces generated during welding.

The above protective lens 50 includes the protective lens fastener 51 having the coupling protrusion 51a formed on one side thereof. One side of the protective lens fastener 51 is penetrated therethrough. The coupling protrusion 51a of the following protective lens fastener 51 is coupled to the coupling recess 24 of the front body 20, so that it can be strongly fixed to the front body 20.

Hereinafter, the method and operation of the mask removable type automatic shading goggles according to the present invention will be described.

In the mask removable type automatic shading goggles according to the present invention, since the mask part 100 having the face protecting cover 120 can be attachably and detachably coupled to the goggle part 200, the worker can wear only the goggle part 200 so as to conducting the welding work. Also, as occasion demands, the cover body is coupled to the front body 20, so that it can protect the worker's face by means of the face protecting cover 120.

At this time, the cover body 110 of the mask part is fixed to the front body 20 of the goggle part 200 by means of the supporting jaw 130 of closely supporting the upper and lower ends of the goggle part 200 thereon. Here, since the cover body 110 is made of elastic material, both sides of the cover body 110 are adhered to the front body 20 through the supporting jaw 130 while being slightly opened to outside.

As described above, when the cover body 110 is coupled to the front body 20, since the supporting jaw 130 formed between the cover body 110 and the face protecting cover 120 is adhered to the lower end of the goggle part 200, it can prevent the harmful light from being leaked into the inside of the goggle part 200. Also, it can prevent the frost from being generated on the protective lens 50 installed on the front surface of the cover body 110 owing to the breath spitted by the worker.

Also, the bending portion of the hooking part 140 formed on the upper portion of the cover body 110 is inserted into and coupled to the upper end of the goggle part 200, thereby more increasing the adhesive force between them.

Moreover, since the locking walls 113 are further formed at both sides of the cover body 110, when the mask part 100 is coupled to the goggle part 200, the locking walls 113 are slid to the rear of the goggle part 200 while being opened to outside, so that they can be elastically coupled to both sides of goggle part 200.

Accordingly, the mask part 100 can be easily attachably and detachably coupled to the goggle part 200 through the supporting jaw 130, the hooking part 140, and the locking walls 113.

Also, when the skirt part 30 is coupled to the rear surface of the goggle part 200, since the skirt part 30 is closely supported thereon, although the worker randomly pulls on the skirt part 30, the soft skirt part 30 is supported by the supporting plate 34 without being torn. Moreover, the soft skirt part 30 can be easily replaced through the screws later on.

Where the worker wears the mask removable type automatic shading goggles according to the present invention and performs the welding operation, if the harmful light (arc) is generated, the light detecting sensor 70 detects the generated harmful light.

Then, the driving signal is generated from the light detecting sensor 70 and then, the control printed circuit board 81 receives the driving signal. Thereafter, the voltage is supplied to the LCD lens 60 to be driven in a pre-set shading degree grade.

Continuously, the worker adjusts the shading degree according to the intensity of the harmful light of the welding operation, so that the shading degree of the LCD lens 60 is adjusted in the welding mode to perform the welding operation.

Here, since the control panel 80 and the power supply 90 installed on both end portions of the goggle part 20 are connected by not the internal power supply line but the electrical connection panel 95 extended to both ends of the goggle part and fixed to the inside body 10, it can prevent the cutoff of the power supply owing to the movement of the power supply line.

Also, the front body 20 further includes ventilation parts 25 protruded toward an upper part and a lower part thereof on the upper and lower surfaces thereof respectively and a plurality of air vents 25*a* formed on one side of the ventilation parts 25 so as to allow the air to be circulated to the inside and outside of the skirt part 30 through the air vents 25*a* during wearing of the automatic shading goggles 1, thereby it can previously prevent the condensation from being occurred on the following LCD lens 60 owing to the heat generated from an eyeball of the worker.

Also, the present invention provides the goggle type, so that the safety helmet, the dust mask, and the earplug essentially required in welding operation can be simultaneously used.

While this invention has been described in connection with what are presently considered to be the most practical and preferred embodiments, it is to be understood that the invention is not limited to the disclosed embodiments and the drawings, but, on the contrary, it is intended to cover various modifications and variations within the spirit and scope of the appended claims.

What is claimed is:

1. A mask removable automatic shading goggles comprising: a goggle part having a liquid crystal display (LCD) lens for blocking a harmful light and configured for protecting a worker's eye installed on an inside of the goggle part and closely worn to a worker's face;
   a mask part having a cover body corresponded to a front surface of the goggle part and attachably and detachably coupled to the front surface of the goggle part, a face protective cover for protecting the worker's face extended to a lower portion of the cover body, and a supporting jaw having a surface bent between the cover body and the face protecting cover and closely supporting an upper end or a lower end of the goggle part;
   a hooking part extended from one side of an upper end of the cover body toward an upper end of the goggle part coupled to an upper end portion of the goggle part; and
   a pair of locking walls as an extending side wall extended from both sides of the cover body to the a rear of the cover body and having exposure holes for exposing both side surfaces of the goggle part to an outside of the mask removable automatic shading goggles, when the mask part is coupled to the goggle part, the pair of locking walls is slid to both sides of the goggle part while being opened to the outside of the mask removable automatic shading goggles, whereby the pair of locking walls is elastically coupled to both sides of the goggle part, wherein the goggle part further comprises a skirt part of a soft material coupled to a rear surface of the goggle part and configured for being adhered to the worker's face, the skirt part comprising a tightly contacting part corresponding to an outer circumference shape of the rear surface of the goggle part and adhered to the rear surface of the goggle part; a coupling part corresponded to the inner surface of the goggle part and protruded from the front surface of the tightly contacting part toward the front part thereof: a curve supporting surface having openings corresponded to a LCD lens at the front surface of the coupling part and extended along an outer circumference of the openings and bent and bordered on the coupling part; and a supporting plate corresponded to the curve supporting surface and closely coupled to the inside of the curve supporting surface.

2. A mask removable automatic shading goggles, comprising:
   a goggle part having a liquid crystal display (LCD) lens for blocking a harmful light and configured for protecting a worker's eye installed on an inside of the goggle part and closely worn to a worker's face;
   a mask part having a cover body corresponded to a front surface of the goggle part and attachably and detachably coupled to the front surface of the goggle part, a face protective cover for protecting the worker's face extended to a lower portion of the cover body, and a supporting jaw having a surface bent between the cover body and the face protecting cover and closely supporting an upper end or a lower end of the goggle part;
   a hooking part extended from one side of an upper end of the cover body toward an upper end of the goggle part coupled to an upper end portion of the goggle part; and
   a pair of locking walls as an extending side wall extended from both sides of the cover body to the a rear of the cover body and having exposure holes for exposing both side surfaces of the goggle part to an outside of the mask removable automatic shading goggles, when the mask part is coupled to the goggle part, the pair of locking walls is slid to both sides of the goggle part while being opened to the outside of the mask removable automatic shading goggles, whereby the pair of locking walls is elastically coupled to both sides of the goggle part, wherein the goggle part further comprises: extending side walls extended from both end portions thereof and the rear thereof; a control panel formed at one side of the side walls, supplying a voltage to the LCD lens, and varying a light transmission of the LCD lens; a power supply formed at one side of the goggle part and supplying a power to the control panel; and an electrical connection panel formed at the inside of the goggle part and having one end electrically connected to the power supply and the other end electrically connected to the control panel, wherein the power is supplied to the LCD lens and the control panel by means of the electrical connection panel.

3. The mask removable automatic shading goggles as claimed in claim 2, wherein the goggle part further comprises:
   an inside body configured for being formed in a shape corresponding to a curvature of a worker's face and having a pair of first extending side walls extended from both sides of the inside body to the rear thereof so as to an installation and first openings formed at the front surface thereof;
   a front body formed at a front surface of the inside body and having second openings corresponding to the first openings and a pair of second extending side walls extended from both sides thereof to the rear thereof and corresponded to the pair of the first extending side walls respectively and first exposure holes formed on one side of the pair of the second extending side walls so as to expose parts of the control panel and the power supply to outside; and the LCD lens for covering the first openings interposed between the inside body and the front body; openings, wherein the front body further comprises at least one ventilation part formed on one side thereof.

4. The mask removable automatic shading goggles as claimed in claim 3, wherein the ventilation part comprises a plurality of air vents formed on the upper and lower portions of the front body or one side of the second extending side walls so as to allow the air to be circulated to the inside and outside of the front body.

* * * * *